United States Patent
Ona et al.

(10) Patent No.: US 6,267,842 B1
(45) Date of Patent: Jul. 31, 2001

(54) WATER-BASED TREATMENT AGENT FOR TISSUE PAPER AND TISSUE PAPER TREATMENT METHOD

(75) Inventors: Isao Ona; Hiroki Ishikawa; Tsutomu Naganawa; Kazuo Kobayashi; Yoshitsugu Morita, all of Chiba Prefecture (JP)

(73) Assignee: Dow Corning Toray Silicone Company, Ltd., Tokyo (JP)

( * ) Notice: Subject to any disclaimer, the term of this patent is extended or adjusted under 35 U.S.C. 154(b) by 0 days.

(21) Appl. No.: 09/575,750

(22) Filed: May 22, 2000

(30) Foreign Application Priority Data

May 24, 1999 (JP) .................................................. 11-143696

(51) Int. Cl.⁷ ............................. D21H 17/33; B05D 3/02; B23B 27/10
(52) U.S. Cl. ........................ 162/135; 162/135; 162/112; 162/158; 162/164.4; 427/387; 427/391; 428/447; 428/452
(58) Field of Search ..................................... 428/447, 452; 162/164.4, 135, 112, 158; 427/387, 391

(56) References Cited

U.S. PATENT DOCUMENTS

| 5,059,282 | 10/1991 | Ampulski et al. | 162/111 |
| 5,164,046 | 11/1992 | Ampulski et al. | 162/111 |
| 6,057,386 | 5/2000 | Morita et al. | 523/212 |

FOREIGN PATENT DOCUMENTS

| 0 347 153 A2 | 12/1989 | (EP) | D21H/3/62 |
| 06311943 | 11/1994 | (JP) | A47K/10/16 |
| 07145596 | 6/1995 | (JP) | A47K/10/16 |

*Primary Examiner*—Harold Pyon
*Assistant Examiner*—Elena Tsoy
(74) *Attorney, Agent, or Firm*—James L. De Cesare

(57) ABSTRACT

A water-based treatment agent for tissue paper suppresses any feeling of slipperiness or wetness in ordinary tissue paper and toilet paper so the paper has a dry touch, ample smoothness, and a clean, smooth, tactile impression. It also provides the paper with a superior softness. The water-based treatment agent consists of a silicone oil emulsion in which crosslinked silicone particles with a mean particle size of 0.01–100 μm are contained in silicone oil droplets with a mean particle size of 0.05–500 μm, which are dispersed in water. The particle size of the crosslinked silicone particles is smaller than the particle size of the silicone oil droplets.

6 Claims, No Drawings

WATER-BASED TREATMENT AGENT FOR TISSUE PAPER AND TISSUE PAPER TREATMENT METHOD

FIELD OF THE INVENTION

This invention is directed to a water-based treatment agent for tissue paper, and to a tissue paper treatment method. More specifically, the invention relates to (i) a water-based treatment agent for tissue paper which can suppress any feeling of slipperiness or wetness in tissue papers such as ordinary tissue paper or toilet paper, so that the papers have a dry touch, ample smoothness, and a clean, smooth, tactile impression, and which provides the paper with superior softness; and (ii) a tissue paper treatment method for obtaining tissue paper having superior softness in which any feeling of slipperiness or wetness is suppressed, so that the paper has a dry touch, ample smoothness, and a clean, smooth, tactile impression.

BACKGROUND OF THE INVENTION

When ordinary tissue paper and toilet paper lacks softness and smoothness, the frequent use of such paper can result in rough, red, and painful skin. Therefore, many methods have been proposed to solve this problem. For example, one technique involves a method in which such tissue paper is treated with a dimethylpolysiloxane or a dimethylpolysiloxane having a functional group such as an amino group, carboxy group, hydroxy group, ether group, polyether group, aldehyde group, ketone group, amido group, ester group, or thiol group, and this method is described in Japanese Patent Application Kokai No. Hei 2-224626, and Japanese Patent Application Kokai No. Hei 3-900, the English equivalents of which are EP 347153, U.S. Pat. Nos. 5,059,282, and 5,164,046. Another technique involves a method in which such papers are treated with an emulsion of an organopolysiloxane containing amino groups, and a diorganopolysiloxane containing polyether groups, and this method is described in Japanese Patent Application Kokai No. Hei 6-311943. Other known techniques include a method in which such papers are treated with a diorganopolysiloxane and a polyhydric alcohol, as described in Japanese Patent Application Kokai No. Hei 7-145596.

However, it has been found that tissue paper treated according to these methods does not have satisfactory softness, but that the paper has a rough feeling and an unsatisfactory hand. This is especially true when the paper is treated with a diorganopolysiloxane containing an amino group, in which case, an excessively slippery feeling is produced, so that the sensation produced by contact with the skin of the hands is unsatisfactory. Furthermore, when the paper is treated with a diorganopolysiloxane containing a polyether group, the smoothness and slipping sensation is unsatisfactory.

BRIEF SUMMARY OF THE INVENTION

Therefore, the object of the present invention is to provide
(i) a water-based treatment agent for tissue paper which suppresses any feeling of slipperiness or wetness in tissue paper such as ordinary tissue paper or toilet paper, so that the paper has a dry touch, ample smoothness, and a clean, smooth, tactile impression, and which imparts paper with superior softness; and
(ii) a tissue paper treatment method for obtaining tissue paper having superior softness in which any feeling of slipperiness or wetness is suppressed, so that the paper has a dry touch, ample smoothness, and a clean, smooth, tactile impression.

The water-based treatment agent for tissue paper is characterized by it being an agent consisting of a silicone oil emulsion in which crosslinked silicone particles with a mean particle size of 0.01–100 µm are contained in silicone oil droplets with a mean particle size of 0.05–500 µm, which are dispersed in water. The particle size of the crosslinked silicone particles is smaller than the particle size of the silicone oil droplets.

Likewise, the tissue paper treatment method is characterized by it being one in which tissue paper is treated with a water-based treatment agent for tissue paper which consists of a silicone oil emulsion in which crosslinked silicone particles with a mean particle size of 0.01–100 µm are contained in silicone oil droplets with a mean particle size of 0.05–500 µm, which are dispersed in water. Again the particle size of the crosslinked silicone particles is smaller than the particle size of the silicone oil droplets.

These and other features of the invention will become apparent from a consideration of the detailed description.

BRIEF DESCRIPTION OF THE SEVERAL VIEWS OF THE DRAWING

Not applicable.

DETAILED DESCRIPTION OF THE INVENTION

The water-based treatment agent for tissue paper according to this invention consists of a silicone oil emulsion in which crosslinked silicone particles are contained in silicone oil droplets that are dispersed in water. In this emulsion, the crosslinked silicone particles are obtained by crosslinking a crosslinkable silicone composition.

Examples of crosslinkable silicone compositions include compositions crosslinked by a hydrosilylation crosslinking reaction, compositions crosslinked by a condensation crosslinking reaction, compositions crosslinked by an organic peroxide crosslinking reaction, and compositions crosslinked by a high-energy radiation crosslinking reaction. Most preferred are compositions crosslinked by hydrosilylation crosslinking reactions and compositions crosslinked by condensation crosslinking reactions.

In the emulsion, there are no limitations on the type of silicone oil used to form the silicone oil droplets, but it is preferred that the silicone oil be a silicone oil with a linear molecular structure, a linear molecular structure with some degree of branching, a cyclic molecular structure, or a branched molecular structure. Silicone oils with linear molecular structure are most preferred. The silicone oil should be a silicone oil that does not participate in the crosslinking reaction that takes place when the crosslinked silicone particles are formed, i.e., a silicone oil that does not undergo a crosslinking reaction and that does not hinder crosslinking reactions.

When the crosslinked silicone particles are obtained by a hydrosilylation crosslinking reaction, the silicone oil should have no alkenyl groups or hydrogen atoms bonded to silicon atoms in its molecule. Some representative examples include dimethylpolysiloxanes in which both ends of the molecular chain are terminated with trimethylsiloxy groups, methylphenylpolysiloxanes in which both ends of the molecular chain are terminated with trimethylsiloxy groups, dimethylsiloxane/methylphenylsiloxane copolymers in which both ends of the molecular chain are terminated with trimethylsiloxy groups, dimethylsiloxane-methyl (3,3,3-trifluoropropyl) siloxane copolymers in which both ends of the molecular chain are terminated with trimethylsiloxy groups, cyclic dimethylsiloxanes, cyclic methylphenylsiloxanes, and silicone oils in which hydrogen atoms in hydrocarbon groups on side chains and ends of the silicone oil are substituted by epoxy groups, carboxyl groups or polyether groups.

When the crosslinked silicone particles are obtained by a condensation crosslinking reaction, the silicone oil should have no silanol groups, hydrogen atoms bonded to silicon atoms, or hydrolyzable groups bonded to silicon atoms in its molecule. Some representative examples of suitable silicone oils are dimethylpolysiloxanes in which both ends of the molecular chain are terminated with trimethylsiloxy groups, methylphenylpolysiloxanes in which both ends of the molecular chain are terminated with trimethylsiloxy groups, dimethylsiloxane/methylphenylsiloxane copolymers in which both ends of the molecular chain are terminated with trimethylsiloxy groups, dimethylsiloxane-methyl (3,3,3-trifluoropropyl) siloxane copolymers in which both ends of the molecular chain are terminated with trimethylsiloxy groups, cyclic dimethylsiloxanes, cyclic methylphenylsiloxane, dimethylpolysiloxanes in which both ends of the molecular chain are terminated with dimethylvinylsiloxy groups, dimethylsiloxane/methylvinylsiloxane copolymers in which both ends of the molecular chain are terminated with dimethylvinylsiloxy groups, methylvinylpolysiloxanes in which both ends of the molecular chain are terminated with trimethylsiloxy groups, cyclic methylvinylsiloxane, and silicone oils in which hydrogen atoms of hydrocarbon groups on the side chains and ends of the silicone oil are substituted by amino groups, amido groups, epoxy groups, carboxyl groups, or polyether groups.

While there's no limitation on the viscosity of the silicone oil, it should be in the range of 1–100,000,000 mPa·s at 25° C. Preferred is a range of 5–10,000,000 mPa·s. In the emulsion, the mean particle size of the silicone oil droplets should be in the range of 0.05–500 μm, preferably in the range of 0.05–200 μm. The stability of the emulsion as a water-based treatment agent tends to decrease if the mean particle size of the silicone oil droplets is less than the lower limit of the range, or more than its upper limit.

In the emulsion, the mean particle size of crosslinked silicone particles should be in the range of 0.01–100 μm, preferably in the range of 0.05–50 μm. Again, the stability of the emulsion as a water-based treatment agent tends to decrease if the mean particle size of crosslinked silicone particles is less than the lower limit of the range, or more than its upper limit. The mean particle size of crosslinked silicone particles is of course smaller than the mean particle size of silicone oil droplets. The shape of the crosslinked silicone particles may be spherical, spindle-shaped, flat, or amorphous, but a spherical shape is preferred. As to the physical nature of the crosslinked silicone particles, they may have an elastomer gel or rubber form.

For preparing silicone oil emulsions, two methods were considered. In one method, crosslinked silicone particles were uniformly dispersed in a silicone oil, and then the dispersion was emulsified in water. In a second method, the silicone oil emulsion was prepared by first emulsifying a silicone oil in water, preparing a crosslinked silicone particle suspension by emulsifying crosslinked silicone particles in water, and then mixing the two together. However, it was found that in the first method, that the crosslinked silicone particles were not uniformly dispersed in the silicone oil, and as a result, it was difficult to prepare a silicone oil emulsion in which crosslinked silicone particles are contained in silicone oil droplets dispersed in water. In the second method in which crosslinked silicone particles and silicone oil droplets were independently dispersed, it was difficult to prepare a silicone oil emulsion in which crosslinked silicone particles were contained in silicone oil droplets dispersed in water.

Therefore, in the method according to this invention, a crosslinkable silicone composition containing a non-crosslinkable silicone oil is dispersed in water, and then the crosslinking reaction is conducted. In this technique, the content of the non-crosslinkable silicone oil should exceed the amount of the non-crosslinkable silicone oil that can be held by the crosslinked product of the crosslinkable silicone composition.

The crosslinkable silicone composition should be a composition capable of forming an elastomeric type crosslinked product such as a gel or a rubber as a result of the crosslinking reaction. Some examples of suitable compositions include those compositions that are crosslinked by a hydrosilylation crosslinking reaction, compositions that are crosslinked by a condensation crosslinking reaction, compositions that are crosslinked by an organic peroxide crosslinking reaction, and compositions that are crosslinked by a high-energy radiation crosslinking reaction. Preferably, the composition is one crosslinked by a hydrosilylation crosslinking reaction (A) or a condensation crosslinking reaction (B).

One example of such a crosslinkable silicone composition (A) is one crosslinked by a hydrosilylation crosslinking reaction and consisting of at least (i) an organopolysiloxane having at least two alkenyl groups per molecule, (ii) an organopolysiloxane having at least two hydrogen atoms bonded to silicon atoms in each molecule, and (iii) a hydrosilylation reaction catalyst.

Some examples of alkenyl groups in organopolysiloxane (i) include vinyl groups, allyl groups, butenyl groups, pentenyl groups, and hexenyl groups, with vinyl groups being preferred. In organopolysiloxane (i), groups other than alkenyl groups may be bonded to silicon atoms including monovalent hydrocarbon groups such as the alkyl groups methyl, ethyl, propyl, and butyl; cycloalkyl groups such as cyclopentyl and cyclohexyl; aryl groups such as phenyl, tolyl, and xylyl; aralkyl groups such as benzyl, phenethyl, and 3-phenylpropyl; and halogenated hydrocarbon groups such as 3-chloropropyl and 3,3,3-trifluoropropyl.

The molecular structure of organopolysiloxane (i) can be linear, cyclic, a network, or linear with some degree of branching. To obtain crosslinked silicone particles having elastomer form such as a gel or rubber, the molecular structure should be linear or linear with some degree of branching. While there are no limitations on the viscosity of organopolysiloxane (i), it should be a viscosity allowing dispersion of the crosslinkable silicone composition in water. Thus, a viscosity in the range of 20–100,000 mPa·s at 25° C. is preferred, while range of 20–10,000 mPa·s is most preferred.

With regard to organopolysiloxane (ii), some examples of groups other than hydrogen atoms bonded to silicon atoms which can be bonded to silicon atoms include the same monovalent hydrocarbon groups described above. Furthermore, the molecular structure of organopolysiloxane (ii) may also be linear, cyclic, a network, or linear with some degree of branching. The viscosity of organopolysiloxane (ii) should be sufficient to allow dispersion of the crosslinkable silicone composition in water, and a range of 1–10,000 mPa·s at 25° C. is therefore preferred. The amount of organopolysiloxane (ii) mixed with the composition can be any amount sufficient to cure the crosslinkable silicone composition, and it is preferred that the amount be in the range of 0.3–200 parts by weight per 100 parts by weight of the organopolysiloxane (i).

In crosslinkable silicone composition (A), the hydrosilylation reaction catalyst (iii) is used to promote the crosslinking reaction and is preferably a platinum type catalyst. Examples of platinum type catalysts include chloroplatinic acid, alcohol solutions of chloroplatinic acid, olefin complexes of platinum, alkenylsiloxane complexes of platinum, platinum black, and platinum type catalysts supported on silica.

In preparing crosslinkable silicone composition (A), the hydrosilylation reaction catalyst (iii) may be added and dispersed in water with the other ingredients, or the crosslinkable silicone composition without a catalyst can first be dispersed in water and the catalyst then added to water, but in either case, the crosslinkable silicone composition (A) containing the hydrosilylation reaction catalyst is prepared in water. This aqueous dispersion of hydrosilylation reaction catalyst should contain particles of catalyst dispersed with a mean particle size of 1 µm or less. The amount of hydrosilylation reaction catalyst should be sufficient to promote crosslinking reactions of crosslinkable silicone compositions (A). When the catalyst is a platinum type, the amount of platinum metal should constitute $1 \times 10^{-7}$ to $1 \times 10^{-3}$ parts weight per 100 parts by weight of organopolysiloxane (i).

Crosslinkable silicone compositions of the condensation crosslinking reaction type (B) include compositions consisting of at least one organopolysiloxane (iv) having hydroxy groups or hydrolyzable groups such as alkoxy groups, oxime groups, acetoxy groups, or aminoxy groups, bonded to at least two silicon atoms in each molecule, a silane crosslinking agent (v) having hydrolyzable groups such as alkoxy groups, oxime groups, acetoxy groups, or aminoxy groups, bonded to at least three silicon atoms in each molecule, and a condensation reaction catalyst (vi) such as an organo-tin compound or an organo-titanium compound.

For organopolysiloxane (iv), some examples of alkoxy groups are methoxy, ethoxy, and methoxyethoxy. Some examples of oxime groups are dimethylketoxime and methylethylketoxime. In organopolysiloxane (iv), other groups can be bonded to silicon atoms including monovalent hydrocarbon groups such as the alkyl groups of methyl, ethyl, propyl, and butyl; cycloalkyl groups such as cyclopentyl and cyclohexyl; aryl groups such as phenyl, tolyl, and xylyl; aralkyl groups such as benzyl, phenethyl, and 3-phenylpropyl; and halogenated hydrocarbon groups such as 3-chloropropyl and 3,3,3-trifluoropropyl. The molecular structure of organopolysiloxane (iv) can be linear, cyclic, a network, or linear with some degree of branching. However, to form elastomeric type crosslinked silicone particles such as a gels or rubbers, the molecular structure should be linear or linear with some degree of branching. The viscosity of organopolysiloxane (iv) should be sufficient to allow dispersion of the crosslinkable silicone composition (B) in water, and a viscosity in the range of 20–100,000 mPa·s at 25° C. is preferred, with 20–10,000 mPa·s being most preferred.

In silane crosslinking agent (v), the alkoxy and oxime groups can be the same as the groups described above. Some examples of silane crosslinking agents (v) include methyltrimethoxysilane, vinyltrimethoxysilane, methyltrioximesilane, and vinyltrioximesilane. The amount of silane crosslinking agent (v) that is added can be any amount sufficient to cause curing of crosslinkable silicone composition (B). For example, the amount can be 0.3–200 parts by weight per 100 parts by weight of organopolysiloxane (iv).

Condensation reaction catalyst (vi) is an organo-tin or organo-titanium compound, and it is used to promote the crosslinking reaction of crosslinkable silicone composition (B). Some examples of suitable catalysts include dibutyltin dilaurate, dibutyltin diacetate, tin octenoate, dibutyltin dioctate, tin laurate, tetrabutyl titanate, tetrapropyl titanate, and titanium dibutoxybis(ethylacetoacetate). The amount of condensation reaction catalyst (vi) should be sufficient to cause crosslinking of crosslinkable silicone composition (B), and it is preferred to use 0.01–5 parts by weight per 100 parts by weight of organopolysiloxane (iv), and 0.05–2 parts by weight is most preferred.

Fillers can be added to crosslinkable silicone composition (B) as an optional component to adjust the fluidity of the composition, or to increase the mechanical strength of the crosslinked silicone particles obtained. Some examples are reinforcing fillers such as precipitated silica, fumed silica, calcined silica, and fumed titanium oxide; non-reinforcing fillers such as powdered quartz, diatomaceous earth, alumino silicates, iron oxide, zinc oxide, and calcium carbonate; and fillers obtained by treating the surfaces of such materials with organosilicon compounds such as hexamethylsilane, trimethylchlorosilane, polydimethylsiloxane, or polymethyldihydridosiloxane.

The non-crosslinkable silicone oil contained in the crosslinkable silicone composition should be one that does not participate in the crosslinking reaction. The viscosity of the non-crosslinkable silicone oil should be sufficient to allow dispersion of the crosslinkable silicone composition in water. Thus, the preferred viscosity is 1–100,000,000 mPa·s at 25° C., and 2–10,000,000 mPa·s is most preferred. Its molecular structure can be linear, linear with some degree of branching, cyclic, or branched. Linear and cyclic molecular structures are preferred.

For a crosslinkable silicone composition (A) which is the hydrosilylation crosslinking reaction type composition, the non-crosslinkable silicone oil should be one that does not contain alkenyl groups or hydrogen atoms bonded to silicon atoms in the molecule. Some examples of suitable oils are dimethylpolysiloxanes in which both ends of the molecular chain are terminated with trimethylsiloxy groups, methylphenyl polysiloxanes in which both ends of the molecular chain are terminated with trimethylsiloxy groups, dimethylsiloxane/methylphenylsiloxane copolymers in which both ends of the molecular chain are terminated with trimethylsiloxy groups, dimethylsiloxane-methyl (3,3,3-trifluoropropyl) siloxane copolymers in which both ends of the molecular chain are terminated with trimethylsiloxy groups, cyclic dimethylsiloxane, cyclic methylphenylsiloxane, and silicone oils in which hydrogen atoms of hydrocarbon groups on side chains or ends of the oil have been substituted by epoxy, carboxy, or polyether groups.

For crosslinkable silicone composition (B) which is a condensation crosslinking reaction type composition, the non-crosslinkable silicone oil should be one that does not contain silanol groups, hydrogen atoms bonded to silicon atoms, or hydrolyzable groups bonded to silicon atoms in the molecule. Some suitable oils are dimethylpolysiloxanes in which both ends of the molecular chain are terminated with trimethylsiloxy groups, methylphenylpolysiloxanes in which both ends of the molecular chain are terminated with trimethylsiloxy groups, dimethylsiloxane/ methylphenylsiloxane copolymers in which both ends of the molecular chain are terminated with trimethylsiloxy groups, dimethylsiloxane-methyl (3,3,3-trifluoropropyl) siloxane copolymers in which both ends of the molecular chain are terminated with trimethylsiloxy groups, cyclic dimethylsiloxane, cyclic methylphenylsiloxane, dimethylpolysiloxanes in which both ends of the molecular chain are terminated with dimethylvinylsiloxy groups, dimethylsiloxane/methylvinylsiloxane copolymers in which both ends of the molecular chain are terminated with dimethylvinylsiloxy groups, methylvinylpolysiloxanes in which both ends of the molecular chain are terminated with trimethylsiloxy groups, cyclic methylvinylsiloxane, and silicone oils in hydrogen atoms of hydrocarbon groups on side chains and ends of the oil are substituted by amino, amido, epoxy, carboxy, or polyether groups.

The amount of non-crosslinkable silicone oil in the crosslinkable silicone composition should exceed the amount that can be held by the crosslinked product of the crosslinkable silicone composition, i.e., the amount of non-crosslinkable silicone oil that can be contained in the crosslinked product. It will vary according to the particular combination of crosslinkable silicone composition and non-crosslinkable silicone oil, but generally, the amount of non-crosslinkable silicone oil should be in the range of 200–5,000 parts by weight, and preferably 250–2,000 parts by weight, per 100 parts by weight of crosslinkable silicone composition.

In preparing emulsions according to this invention, the crosslinkable silicone composition containing the non-crosslinkable silicone oil is dispersed in water, and the resulting composition is subjected to a crosslinking reaction. An emulsifying device can be used to disperse the crosslinkable silicone composition in water. Some suitable devices include a homomixer, paddle mixer, Henschel mixer, homodisperser, colloid mixer, propeller agitator, homogenizer, in-line continuous emulsifying machine, ultrasonic emulsifier, or vacuum type kneading machine.

The amount of water should be in the range of 5–99 weight percent of the total emulsion, and an amount in the range of 10–80 weight percent is preferred. If desired, a nonionic surfactant, cationic surfactant, or anionic surfactant, can be used to achieve a thorough dispersion of the crosslinkable silicone composition in water and good stability. A nonionic surfactant is preferred. It should be used in the range of 0.1–20 parts by weight per 100 parts by weight of crosslinkable silicone composition containing the non-crosslinkable oil, and 0.5–10 parts by weight is preferred.

When the crosslinkable silicone composition has been dispersed in water, it can be crosslinked by heating it, allowing it to stand at room temperature, or irradiating it with high-energy radiation.

One or more optional components can be added to treatment agents of this invention. Some examples of suitable optional components include organic oils and slip agents such as liquid paraffin, magnesium stearate, and calcium stearate; moisturizing agents such as ethylene glycol, polyethylene glycols with molecular weights of 100–200, diethylene glycol, triethylene glycol, propylene glycol, glycerol, pentaerythritol, sorbitol, mannitol, glucose, sucrose, fructose, or gluconic acid $CH_2OH(CH_2O)_4COOH$; silane or organic antimicrobial agents such as quaternary ammonium salts; tin catalysts such as dibutyltin diacetate and dibutyltin dilaurate; condensation reaction catalysts such as zinc or zirconium catalysts; anti-static agents; static-inhibiting agents; preservatives; anti-rust agents; and fragrances.

Various techniques can be used in treating tissue paper with water-based treatment agents of the invention. For example, the water-based treatment agent can be diluted with water and sprayed directly onto tissue paper, and the tissue paper dried. In another method, the water-based treatment agent can be added to a pulp suspension during the papermaking process. The water-based treatment agent can also be applied by spraying during a pulp drying process or immediately prior to pulp drying. Yet another method can be used in which the water-based treatment agent is caused to adhere to tissue paper by a kiss roll or gravure coater, after which the paper is dried.

The amount of treatment agent used should be such that silicone components in the water-based treatment agent, i.e., the total amount of crosslinked silicone particles and silicone oil, constitutes 0.2–5.0 weight percent of tissue paper, preferably 0.5–3.0 weight percent. When the treatment is performed by spraying the water-based treatment agent directly onto tissue paper and then drying it, drying is performed by heating the paper to a temperature of 50–150° C.

WORKING EXAMPLES

The water-based treatment agent for tissue paper and a tissue paper treatment method are described in the following working examples. Viscosity measurements in these examples were determined at 25° C. Procedures for determining mean particle size of silicone oil droplets, and mean particle size of crosslinked silicone particles in silicone oil emulsions used as water-based treatment agents for tissue paper are set forth below.

Mean Particle Size of Silicone Oil Droplets in Silicone Oil Emulsion

Droplets of silicone oil in the silicone oil emulsion were measured with a laser diffraction particle size distribution measuring device Model LA-500 of Horiba Seisakusho. The median diameter of silicone oil droplets obtained was the particle size corresponding to 50 percent of the cumulative distribution. It was used as the mean particle size.

Mean Particle Size of Crosslinked Silicone Particles in Silicone Oil Emulsion

The silicone oil emulsion was air-dried on a glass plate to remove the water, and crosslinked silicone particles dispersed in the silicone oil were collected and observed with an electron microscope. The average particle size of 10 particles was used as the mean particle size.

Reference Example 1

First, a silicone composition was prepared by mixing together 18.8 parts by weight of a dimethylpolysiloxane with a viscosity of 400 mPa.s in which both ends of the molecular chain were terminated with dimethylvinylsiloxy groups, 1.2 parts by weight of a dimethylsiloxane/ methylhydridosiloxane copolymer with a viscosity of 30 mPa.s in which both ends of the molecular chain were terminated with trimethylsiloxy groups and having at least two hydrogen atoms bonded to silicon atoms in each molecule so the content of hydrogen atoms bonded to silicon atoms was 0.5 weight percent, and 80 parts by weight of a dimethylpolysiloxane with a viscosity of 1,000 mPa.s in which both ends of the molecular chain were terminated with trimethylsiloxy groups. 53 parts by weight of a 3 weight percent aqueous solution of polyoxyethylene nonylphenyl ether with an HLB of 13.1 was added to the silicone composition, to produce an aqueous emulsion.

A separately prepared aqueous emulsion of platinum catalyst consisting of 1,3-divinyl-1,1,3,3- tetramethyldisiloxane complex of platinum with mean particle size of platinum of 0.05 µm and platinum metal concentration of 0.05 weight percent, was uniformly mixed with the silicone emulsion composition in an amount such that the content of platinum metal was 200 ppm by weight, relative to dimethylpolysiloxane in which both ends of the molecular chain were terminated with dimethylvinylsiloxy groups, contained in the emulsion. The result of this procedure was an aqueous emulsion of a crosslinkable silicone composition.

This emulsion was allowed to stand for one day at room temperature so that the crosslinkable silicone composition was caused to undergo hydrosilylation crosslinking reaction, producing a silicone oil emulsion in which crosslinked silicone particles were contained in silicone oil droplets dispersed in water. The mean particle size of silicone oil droplets in the emulsion was 8 µm, and the mean particle size of crosslinked silicone particles contained in the droplets was 3 µm.

The emulsion was transferred to an aluminum dish with a diameter of 5 cm and air dried for 3 days in a draft to remove water, and a creme silicone composition consisting of silicone oil and crosslinked silicone particles was obtained. When the silicone composition was observed under a stereomicroscope, it was found that rubber like crosslinked silicone particles were uniformly dispersed in the silicone oil, and that the shape of the particles was spherical.

Reference Example 2

A silicone oil emulsion in which crosslinked silicone particles were contained in silicone oil droplets dispersed in water was prepared in the same manner as in Reference Example 1, except that 80 parts by weight of dimethylpolysiloxane with a viscosity of 10 mPa.s in which both ends of the molecular chain were terminated with trimethylsiloxy groups, was substituted for the 80 parts by weight of dimethylpolysiloxane with viscosity of 1,000 mPa·s in which both ends of the molecular chain were terminated with trimethylsiloxy groups. The mean particle size of silicone oil droplets in the resulting emulsion was 7 µm, and the mean particle size of crosslinked silicone particles contained in the droplets was 3 µm. Water was removed from the emulsion in the same manner as in Reference Example 1, and a creme silicone composition consisting of silicone oil and crosslinked silicone particles was obtained. When it was observed under a stereomicroscope, it was found that rubber like crosslinked silicone particles were uniformly dispersed in silicone oil, and the shape of particles was spherical.

Reference Example 3

A silicone oil emulsion was prepared by mixing 400 parts by weight of a dimethylpolysiloxane with a viscosity of 1,000 mPa·s in which both ends of the molecular chain were terminated with trimethylsiloxy groups, 20 parts by weight of polyoxyethylene (5) lauryl ether, 10 parts by weight of polyoxyethylene (8.5) nonylphenyl ether, 5 parts by weight of polyoxyethylene (4) nonylphenyl ether sulfonic acid sodium salt, and 565 parts by weight of water. The mixture was then emulsified using a colloid mill.

Reference Example 4

A silicone oil emulsion was prepared by mixing 400 parts by weight of a dimethylpolysiloxane with a viscosity of 10 mPa.s in which both ends of the molecular chain were terminated with trimethylsiloxy groups, 20 parts by weight of polyoxyethylene (5) lauryl ether, 10 parts by weight of polyoxyethylene (8.5) nonylphenyl ether, 5 parts by weight of polyoxyethylene (4) nonylphenyl ether sulfonic acid sodium salt, and 565 parts by weight of water. The mixture was emulsified using a colloid mill, and then further emulsified in a single pass through a homogenizer at 400 kgf/m².

Procedures for the treatment of tissue paper and the evaluations of treated tissue paper are set forth below.

Hand

A commercial grade tissue paper was used composed of two superimposed sheets, each having a longitudinal dimension of 197 mm and a lateral dimension of 229 mm. The paper was confirmed by fluorescent X-ray analysis to be free of adhering silicone, and spread on a metal mesh. The water-based treatment agent for tissue paper was sprayed onto the top and bottom surfaces of the paper using a spray gun under an air pressure of 0.5 kg/cm². The agent was applied until the amount of adhering silicone components was equal to 1.0 weight percent of the tissue paper. The tissue paper with adhering treating agent was dried at 130° C. in a drier for 5 minutes. Five sheets of tissue paper treated in this manner were folded together, and hand was checked by touching the tissue paper with the fingers.

Nose Rubbing Property

One sheet of tissue paper treated as described above was folded in two, and skin around the nose was rubbed strongly 10 times at 5-minute intervals. The condition of the skin was observed by visual inspection. Results were evaluated using the following criteria which is shown in Table 1:

O=No change in skin.
Δ=Skin slightly reddened.
x=Skin somewhat reddened.
O~Δ=Skin slightly reddened but showing no change.

Water Absorption

One drop of water was dropped from a dropper onto tissue paper treated as described above, and the time in seconds required for the water drop to be absorbed by the tissue paper was measured.

Comprehensive Evaluation

The overall suitability of water-based treatment agents for tissue paper was evaluated on the basis of results above using the following criteria which are also shown in Table 1:
O=Optimal.
Δ=Somewhat suitable.
x=Unsuitable.
O~Δ=Suitable but may be unsuitable in some cases.
Δ~x=Unsuitable but may be suitable in some cases.

Working Examples 1 & 2, Comparative Examples 1 & 2, & Blank

Tissue paper was treated by the above method using the silicone oil emulsion prepared in Reference Example 1 as water-based treatment agent (A) for tissue paper. Tissue paper was treated by the above method using the silicone oil emulsion prepared in Reference Example 2 as water-based treatment agent (B) for tissue paper. For comparison, tissue paper was treated by the above method using the silicone oil emulsion prepared in Reference Example 3 as water-based treatment agent (C) for tissue paper. Another comparison was tissue paper treated by the above method using the silicone oil emulsion prepared in Reference Example 4 as water-based treatment agent (D) for tissue paper. As a blank, a commercial grade tissue paper composed of two superimposed sheets with a longitudinal dimension of 197 mm and a lateral dimension of 229 mm was employed. The paper was confirmed by fluorescent X-ray analysis to be free of adhering silicone and spread on a metal mesh. Water was sprayed onto the top and bottom surfaces of the paper with a spray gun under an air pressure of 0.5 kg/cm². The tissue paper was then dried for 5 minutes in a drier at 130° C. The hand, nose rubbing property, and water absorption of these tissue papers were evaluated, and the results are shown in Table 1.

TABLE 1

| Item | Working Ex. 1 | Working Ex. 2 | Comparison Example 1 | Comparison Example 2 | Blank Test |
|---|---|---|---|---|---|
| H2O base treating agent, tissue paper | A | B | C | D | Only H2O |
| Hand | Smooth feel, good slip & hand | Slight core felt but smooth feel & good slip & hand | Soft bulky feel but not smooth | Felt core, not smooth & not soft | Rough feel & poor hand |
| Nose rub property | ○ | ○ | Δ | Δ~X | X |
| H2O absorbed (sec.) | 0.3 | 0.2 | 0.5 | 0.2 | 0 |
| Overall value | ○ | ○ | Δ | Δ | X |

Working Example 3

A two-ply toilet paper composed of two superimposed sheets was cut to a length of 30 cm and treated in the same manner as in Working Example 1. The treated toilet paper was then used by a volunteer. The slip properties on the skin were found to be good, and the paper was soft and extremely easy to use. There was no deterioration in terms of its wiping characteristics. Furthermore, even after rinsing, the paper dissolved easily in water in the same manner as an untreated toilet paper.

Water-based treatment agents of this invention for tissue paper inhibit slippery feeling or wet feeling in tissue paper such as ordinary tissue paper or toilet paper. It is capable of providing tissue paper with a dry touch, an ample smoothness, a smooth feeling to the touch, and a superior softness. In addition, the tissue paper treatment method produces tissue paper in which slippery or wet feeling are suppressed and which has a dry touch, an ample smoothness, smooth feeling to touch, and superior softness.

Other variations may be made in compounds, compositions, and methods described herein without departing from the essential features of the invention. The embodiments of the invention specifically illustrated herein are exemplary only and not intended as limitations on their scope except as defined in the appended claims.

What is claimed is:

1. A method of treating tissue paper comprising applying to tissue paper a water-based treatment agent, the water-based treatment agent being a silicone oil emulsion in which elastomeric crosslinked silicone particles with a mean particle size of 0.01–100 μm are contained in silicone oil droplets with a mean particle size of 0.05–500 μm, and the silicone oil droplets are dispersed in water, the particle size of elastomeric crosslinked silicone particles being smaller than the particle size of silicone oil droplets.

2. The method according to claim 1 wherein the viscosity of the silicone oil at 25° C. is 1–100,000,000 mPa·s.

3. The method according to claim 1 wherein the elastomeric crosslinked silicone particles are obtained by a hydrosilylation crosslinking reaction or by a condensation crosslinking reaction.

4. The method according to claim 1 wherein the silicone oil emulsion is obtained by dispersing a crosslinkable silicone composition containing a non-crosslinkable silicone oil in water, and conducting a crosslinking reaction, the content of the non-crosslinkable silicone oil being more than the amount of the non-crosslinkable silicone oil that is held by the crosslinked product of the crosslinkable silicone composition.

5. The method according to claim 4 wherein the viscosity of the non-crosslinkable silicone oil 25° C. is 1–100,000,000 mPa·s.

6. The method according to claim 5 wherein the crosslinkable silicone composition is of being crosslinked by a hydrosilylation crosslinking reaction or by a condensation crosslinking reaction.

* * * * *